(12) United States Patent
Yuyama

(10) Patent No.: US 11,046,465 B2
(45) Date of Patent: Jun. 29, 2021

(54) SOLID PREPARATION SUBDIVIDING APPARATUS AND SOLID PREPARATION SELLING METHOD

(71) Applicant: YUYAMA MFG. CO., LTD., Osaka (JP)

(72) Inventor: Hiroyuki Yuyama, Osaka (JP)

(73) Assignee: YUYAMA MFG. CO., LTD., Osaka (JP)

(*) Notice: Subject to any disclaimer, the term of this patent is extended or adjusted under 35 U.S.C. 154(b) by 0 days.

(21) Appl. No.: 16/716,377

(22) Filed: Dec. 16, 2019

(65) Prior Publication Data

US 2020/0115075 A1 Apr. 16, 2020

Related U.S. Application Data

(63) Continuation of application No. PCT/JP2018/026791, filed on Jul. 18, 2018.

(30) Foreign Application Priority Data

Jul. 20, 2017 (JP) .............................. JP2017-140622

(51) Int. Cl.
*G07F 17/00* (2006.01)
*B65B 5/10* (2006.01)
(Continued)

(52) U.S. Cl.
CPC ............ *B65B 5/103* (2013.01); *A61J 7/0084* (2013.01); *A61J 7/0481* (2013.01); *B65B 43/62* (2013.01);
(Continued)

(58) Field of Classification Search
CPC ..... G07F 17/0092; B65B 5/103; B65B 43/62; A61J 7/0084; A61J 7/0481; A61J 2200/30; G16H 20/13
See application file for complete search history.

(56) References Cited

U.S. PATENT DOCUMENTS 8,342,400 B1 * 1/2013 Reese ................... G16H 20/13
235/385
2003/0200726 A1 10/2003 Rast
(Continued)

FOREIGN PATENT DOCUMENTS

JP         H4-87904 A      3/1992
JP         H6-227526 A     8/1994
(Continued)

OTHER PUBLICATIONS

International Search Report in PCT/JP2018/026791, dated Oct. 16, 2018. 4pp.

*Primary Examiner* — Timothy R Waggoner
(74) *Attorney, Agent, or Firm* — Hauptman Ham, LLP

(57) ABSTRACT

A solid preparation subdividing device includes: one or more dispensing devices, a solid preparation information input unit to input information on solid preparations, an administration information input unit, and a packaging unit. The dispensing device includes: an accommodating portion with a charging port to receive solid preparations, and a pickup unit to discharge a desired number of solid preparations from the accommodating portion. The administration information input unit is for directly inputting an administration timing for each solid preparation and a dosage for each administration timing in association with the solid preparations charged into the accommodating portion. The subdividing device executes operations for discharging, based on information input to the administration information input unit, the solid preparations from the dispensing device on a dose-by-dose basis to the packaging unit and packaging one or more kinds of solid preparations to be taken at a time collectively by the packaging unit.

16 Claims, 6 Drawing Sheets

(51) Int. Cl.
*G16H 20/13* (2018.01)
*A61J 7/00* (2006.01)
*A61J 7/04* (2006.01)
*B65B 43/62* (2006.01)

(52) U.S. Cl.
CPC ......... *G07F 17/0092* (2013.01); *G16H 20/13* (2018.01); *A61J 2200/30* (2013.01)

(56) References Cited

U.S. PATENT DOCUMENTS

| | | |
|---|---|---|
| 2009/0289079 A1 | 11/2009 | Yuyama |
| 2015/0039124 A1 | 2/2015 | Mistovich et al. |
| 2015/0090733 A1 | 4/2015 | Park |
| 2015/0190312 A1* | 7/2015 | Yuyama .................. A61J 7/02 700/232 |

FOREIGN PATENT DOCUMENTS

| | | |
|---|---|---|
| JP | 2002-224197 A | 8/2002 |
| JP | 2005-289463 A | 10/2005 |
| JP | 2008-13216 A | 1/2008 |

\* cited by examiner

| NAME | GENNAI HIRAGA | | | |
|---|---|---|---|---|
| PRODUCT NAME | VITAMIN SUPPLEMENT | | | |
| WHEN TO TAKE | AFTER BREAKFAST | AFTER LUNCH | AFTER DINNER | BEFORE BEDTIME |
| NUMBER TO TAKE | | | | |

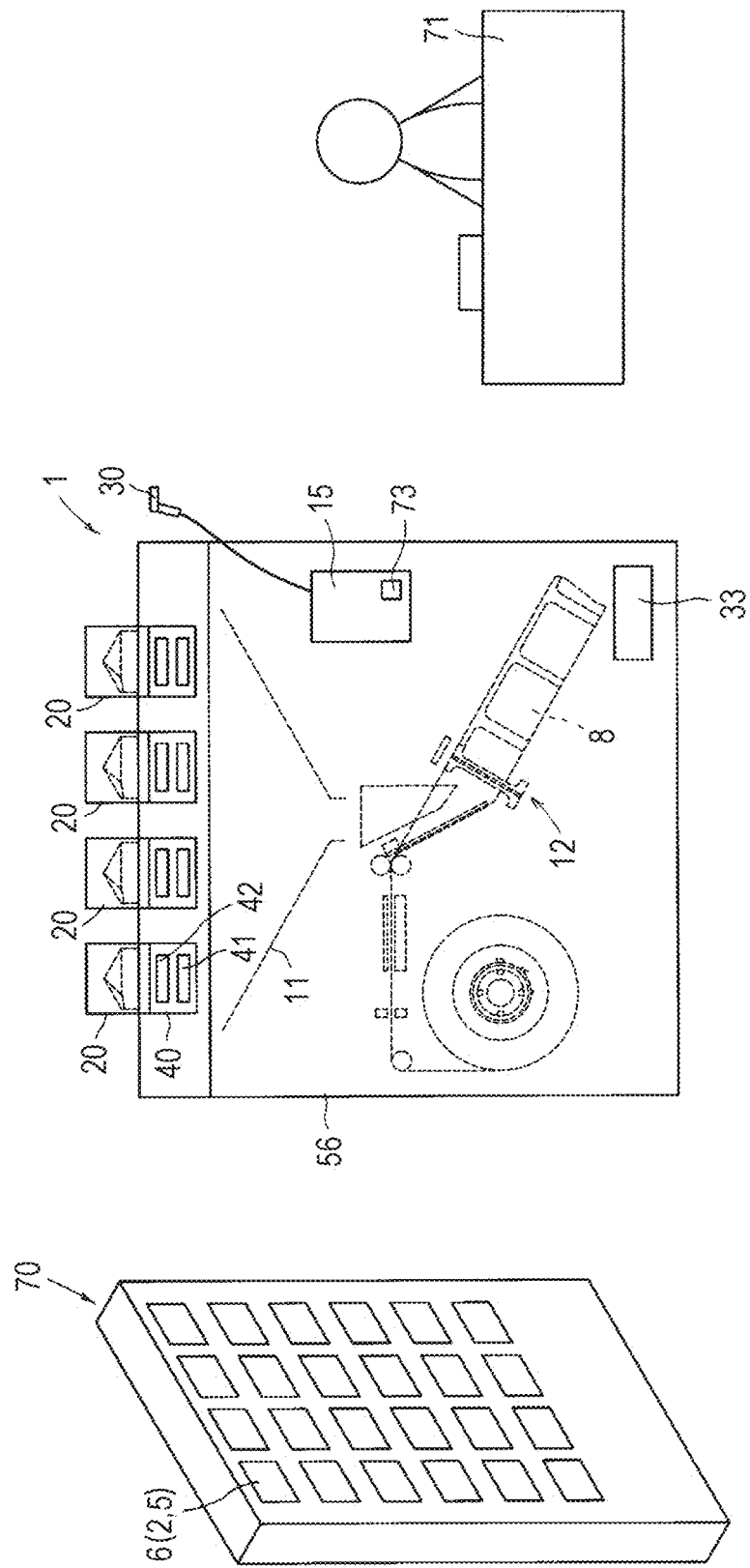

SOLID PREPARATION SUBDIVIDING APPARATUS AND SOLID PREPARATION SELLING METHOD

RELATED APPLICATIONS

The present application is a Continuation of PCT International Application Number PCT/JP2018/026791 filed Jul. 18, 2018, which claims priority of Japanese Application No. 2017-140622, filed Jul. 20, 2017. The above-captioned applications are hereby incorporated by reference herein in their entireties.

TECHNICAL FIELD

This disclosure relates to a device configured to subdivide solid preparations on a dose-by-dose basis. This disclosure relates to a device configured to open a product of solid preparations commercially available by being, for example, packed in a bottle or packed in a pouch, redistribute the solid preparations, and subdivide the solid preparations on a dose-by-dose basis.

Further, this disclosure relates to a solid preparation sales method of opening a packaging material for commercially available solid preparations, redistributing the solid preparations, and subdividing the solid preparations on a dose-by-dose basis for sale.

BACKGROUND ART

For example, there are supplements to be taken for promotion of health. The supplements often do not require a prescription given by a doctor, and can be purchased at a drug store or a convenience store.

Most supplements are shaped into a solid form so as to be easily taken.

Such solid supplements are often commercially available in a packaged form in which a predetermined number of solid supplements, for example, 20 or 50 solid supplements, are packed in a bottle or packed in a pouch.

In general, supplements have a gradual effect on the human body, and there are few restrictions on a dosage or an administration timing. However, even supplements are desired to be taken at a set time and by a set dosage. In addition, people who habitually take supplements are strongly health-oriented in general, and often decide on an administration timing and a dosage themselves.

Hitherto, a recipient purchases desired supplements at a drug store or other such store, and when an administration timing arrives, opens a bottle or a pouch of a product, and picks up a required dosage to take the supplements.

CITATION LIST

Patent Literature

[PTL 1] JP 2008-13216 A
[PTL 2] JP 2005-289463 A

SUMMARY OF INVENTION

Technical Problem

There is a tendency that a person who habitually takes solid supplements takes a plurality of supplements together. In this case, solid supplements are often taken outside at an administration time. Therefore, a recipient puts a pouch or a bottle of a product filled with supplements in a handbag or other such bag and carries the pouch or the bottle around. Some people who habitually take supplements always carry the package pouch or the bottle of the product.

Each package of the supplements is not so large, but a plurality of packages may be bulky when carried together.

Therefore, consumers desire to open the package and subdivide the supplements so that the supplements are easily taken and the package is easily carried around.

This disclosure has an object to provide a device configured to redistribute solid preparations sold by being filled in a small container such as a package pouch or a bottle for individual use and subdivide the solid preparations on a dose-by-dose basis. This disclosure also has an object to provide a solid preparation sales method of subdividing solid preparations for sale as a new business model.

Solution to Problem

In order to solve the above-mentioned problem, according to one aspect of this disclosure, there is provided a solid preparation subdividing device, which is configured to subdivide a plurality of solid preparations on a dose-by-dose basis, the solid preparation subdividing device including: one or a plurality of solid preparation dispensing devices; a solid preparation information input unit configured to input information related to the plurality of solid preparations; an administration information input unit; and a packaging unit, wherein the one or plurality of solid preparation dispensing devices each include: a solid preparation accommodating portion, which has a charging port into which the plurality of solid preparations are to be charged, and is capable of accommodating the plurality of solid preparations; and a solid preparation pickup unit configured to discharge a desired number of solid preparations from the solid preparation accommodating portion, wherein the solid preparation information input unit is configured to input information for identifying the plurality of solid preparations charged into the solid preparation accommodating portion, wherein the administration information input unit is capable of inputting an administration timing for each of the plurality of solid preparations and a dosage for each administration timing in association with the plurality of solid preparations charged into the solid preparation accommodating portion, and wherein the solid preparation subdividing device is configured to execute a series of individual packaging operations for discharging, based on information input to the administration information input unit, the plurality of solid preparations from the one or plurality of solid preparation dispensing devices on a dose-by-dose basis to send out the plurality of solid preparations to the packaging unit and packaging one or a plurality of kinds of solid preparations to be taken at a time collectively by the packaging unit.

In the above-mentioned configuration, it is desired that the solid preparation subdividing device include a printing unit, and the solid preparation subdividing device be configured to perform predetermined printing on a package corresponding to a dose by the printing unit.

In the above-mentioned each configuration, it is desired that the solid preparation subdividing device include a form changing unit configured to change a form of the form changing unit so that the plurality of solid preparations can be smoothly discharged depending on a shape of each of the plurality of solid preparations.

It is desired that the form changing unit be configured to function based on information input to the solid preparation information input unit.

In the above-mentioned configuration, it is desired that the solid preparation subdividing device include a dispensing passage for allowing the plurality of solid preparations to pass therethrough, the form changing unit be capable of restricting a shape of a solid preparation allowed to pass through the dispensing passage by changing a state of the dispensing passage, and the solid preparation subdividing device be configured to change the state of the dispensing passage based on information input to the solid preparation information input unit, to thereby enable the plurality of solid preparations accommodated in the solid preparation accommodating portion of the one or plurality of solid preparation dispensing devices to be discharged.

It is desired that the administration information input unit be formed of one or a plurality of input devices, each of the input devices correspond to any one of the solid preparation dispensing devices, and the solid preparation subdividing device be configured to: identify each of the plurality of solid preparations when input is performed from each of the plurality of input devices; and allow the administration timing for each of the plurality of solid preparations and the dosage for each administration timing to be directly input in association with each other through use of the plurality of input devices.

It is desired that the administration information input unit be mounted to each individual solid preparation dispensing device.

It is desired that the administration information input unit include a display screen, on which a solid preparation display field for identifying each of the plurality of solid preparations and a timing field for displaying the administration timing for each of the plurality of solid preparations are displayed in association with each other along with a number input field corresponding to the administration timing to allow a number to be input to the number input field.

In the above-mentioned each aspect, it is desired that the solid preparation information input unit include a reading unit.

In the above-mentioned each aspect, it is desired that the solid preparation subdividing device include a storage unit, the storage unit be configured to store information for identifying a recipient and the information input to the administration information input unit in association with information input to the solid preparation information input unit, and the solid preparation subdividing device be configured to again execute the series of individual packaging operations based on information stored in the storage unit when solid preparations are again charged from the charging port into the solid preparation accommodating portion after the series of individual packaging operations is executed and the solid preparation information input unit further inputs, into the solid preparation accommodating portion, information for identifying each of the solid preparations charged again.

In the above-mentioned each aspect, it is desired that, in a case in which a plurality of solid preparation dispensing devices are provided, and solid preparations are charged into the plurality of solid preparation dispensing devices, when solid preparations being different solid preparation but having the same administration timing are provided, different solid preparations having the same administration timing be enclosed in the same package.

According to one aspect of this disclosure, there is provided a solid preparation sales method, in which there are a plurality of kinds of commercially available solid preparations, which are commercially available by containing a plurality of solid preparations being the same in a packaging material in advance, the solid preparation sales method including: allowing a purchaser to select desired commercially available solid preparations from among the plurality of kinds of commercially available solid preparations; opening a selected packaging material; subdividing solid drugs that have been opened and taken out for each administration timing, packaging the solid drugs, and passing over the solid drugs; and further deciding a total price of the selected commercially available solid preparations at any one of stages.

In the above-mentioned aspect, it is desired that the solid preparation sales method include using a solid preparation subdividing device, which is configured to subdivide the plurality of solid preparations on a dose-by-dose basis, to charge the solid drugs that have been opened and taken out into the solid preparation subdividing device and subdivide the solid drugs for each administration timing.

In the above-mentioned aspect, it is desired that the solid preparation sales method include using the above-mentioned solid preparation subdividing device to charge the solid drugs that have been opened and taken out into the solid preparation subdividing device and subdivide the solid drugs for each administration timing.

Advantageous Effects of Invention

According to the solid preparation subdividing device of this disclosure, solid preparations sold by being filled in a pouch or a bottle can be redistributed and subdivided on a dose-by-dose basis.

Further, according to the solid preparation sales method of this disclosure, solid preparations can be purchased after having been subdivided on a dose-by-dose basis.

BRIEF DESCRIPTION OF DRAWINGS

FIG. 7 is a conceptual diagram for illustrating a state of a drug store in which the solid preparation subdividing device of FIGS. 6A and 6B are installed.

DESCRIPTION OF EMBODIMENTS

Figure 1:
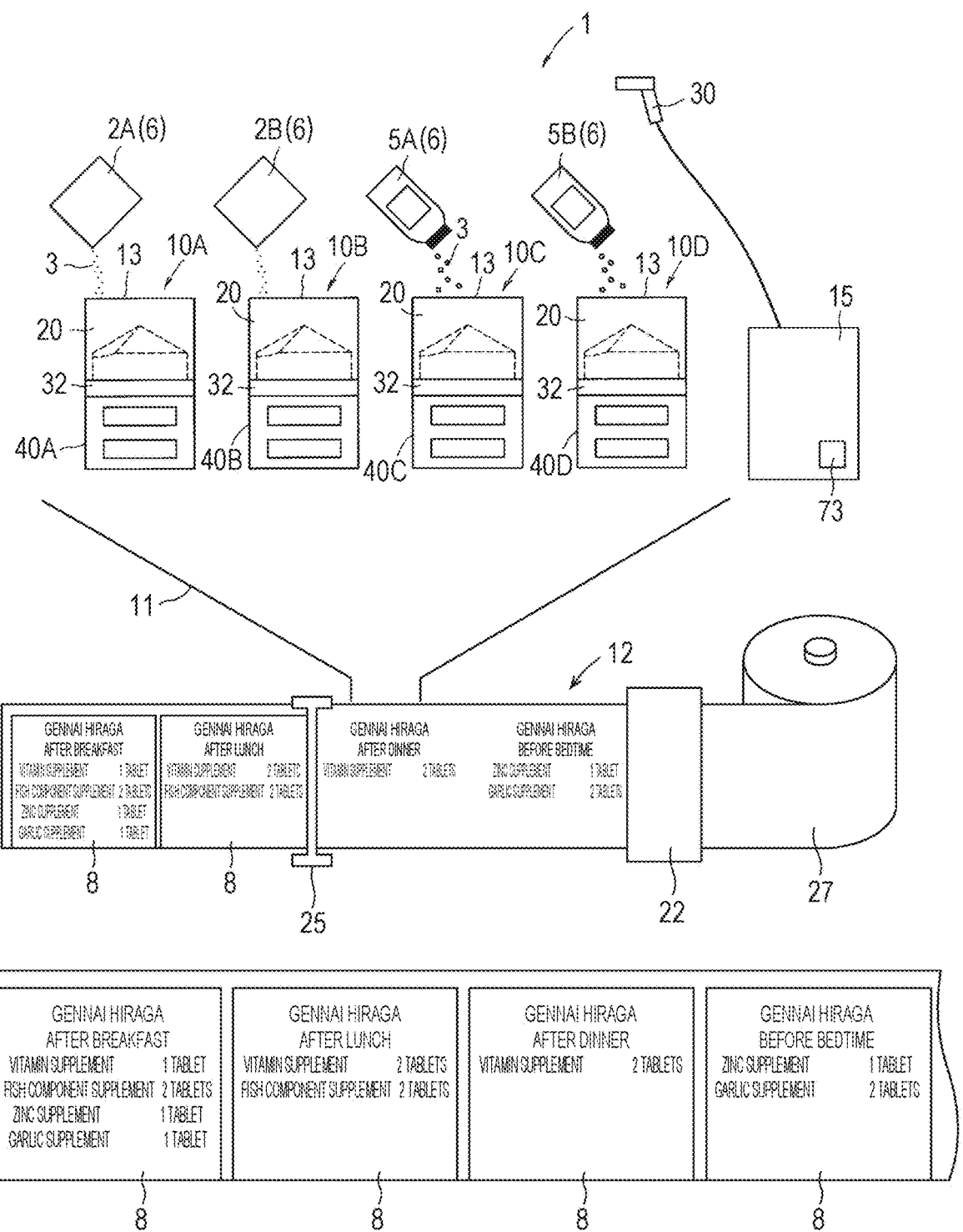
FIG. 1 is a conceptual diagram of a solid preparation subdividing device according to an embodiment of this disclosure.

Now, an embodiment of this disclosure is further described.

A solid preparation subdividing device 1 according to this embodiment is a device configured to subdivide solid preparations 3 sold by being filled in packaging materials 6 such as package pouches 2 and bottles 5 in accordance with administration timings and further package the solid preparations 3 to produce bags (packages) 8 divided on a dose-by-dose basis.

For example, the packaging material 6 is a publicly known container filled with the solid preparations 3, for example, supplements, for the purpose of sales. Representative examples of the packaging material 6 include the package pouch 2 and the bottle 5.

The solid preparation 3 is not limited to the supplement, and may be, for example, any commercially available drug such as a vitamin preparation or a medicine for intestinal disorders.

The package pouch 2 and the bottle 5 of this embodiment are filled with a predetermined number of supplements obtained by preparing ingredients, vitamins, and minerals that have medicinal properties and are useful for promotion of health based on an original prescription given by a producer of the supplements, and shaping the resultant into the solid preparations 3.

The solid preparations 3 targeted by this embodiment, which are packed in the package pouch 2 and packed in the bottle 5, are not prepared for an identified patient or supplement recipient, but are to be displayed in a drug store, a convenience store, or other such store and to be sold to the general public.

In general, the package pouch 2 or the like has a label 17 or the like on which information for identifying a product is recorded. In some cases, the information is directly printed on the package pouch 2 or the like.

In this embodiment, both recording through use of characters and recording through recording means, for example, a barcode, are used together in the label 17. The recording of information may be recording through an electrical method, for example, an IC chip.

In this embodiment, the label 17 is placed on the package pouch 2 and the bottle 5, and characters and a two-dimensional barcode 7 are given on the label 17.

In this embodiment, the two-dimensional barcode 7 functions as an information recording portion.

As character information printed on the label 17, there are given a product name, a component indication showing a solid preparation name or a component, and indications of, for example, a use method and a dosage to be recommended.

Figure 2:
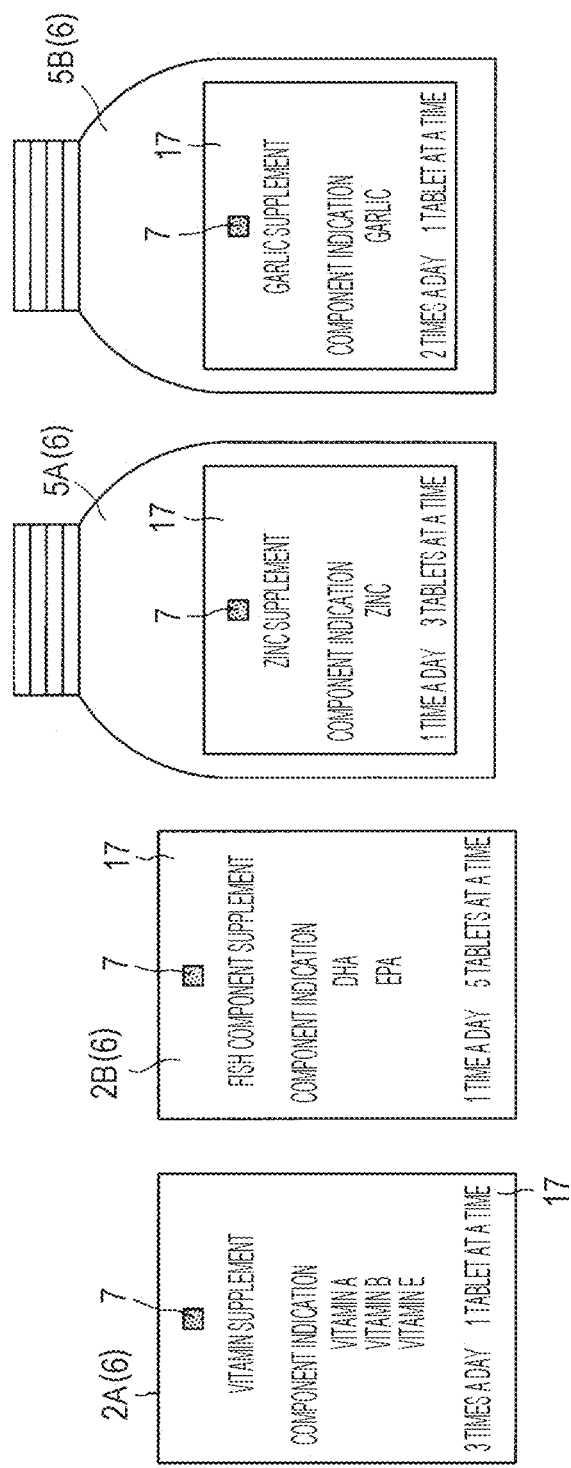
FIG. 2 is a front view for illustrating packaged forms of commercially available solid preparations.

Specifically, as in FIG. 2, on the label (information recording portion) 17 of the package pouch 2A, a character indication of "VITAMIN SUPPLEMENT" is given as the product name, a character indication of "VITAMIN A, VITAMIN B, VITAMIN E" is given as the component indication, and a character indication of "3 TIMES A DAY, 1 TABLET AT A TIME" is given as a recommended use method indication.

On a package pouch 2B, a character indication of "FISH COMPONENT SUPPLEMENT" is given as the product name, a character indication of "DHA, EPA" is given as the component indication, and a character indication of "1 TIME A DAY, 5 TABLETS AT A TIME" is given as a recommended use method indication.

On a bottle 5A, a character indication of "ZINC SUPPLEMENT" is given as the product name, a character indication of "ZINC" is given as the component indication, and a character indication of "1 TIME A DAY, 3 TABLETS AT A TIME" is given as a recommended use method indication.

On a bottle 5B, a character indication of "GARLIC SUPPLEMENT" is given as the product name, a character indication of "GARLIC" is given as the component indication, and a character indication of "2 TIMES A DAY, 1 TABLET AT A TIME" is given as a recommended use method indication.

Moreover, information corresponding to a product name, a component, a use method, and a dosage is written in the two-dimensional barcode 7.

Moreover, when the solid preparation is a drug, identification information of the solid preparation is recorded on the two-dimensional bar code 7.

The identification information is information capable of identifying a kind of a solid preparation (drug), and examples thereof include a drug name, a drug ID, a drug code, a JAN code, an RSS code, and an OR code (trademark).

In some cases, the identification information is recorded separately from the two-dimensional barcode 7 described above.

The solid preparation subdividing device 1 according to this embodiment includes a plurality of solid preparation dispensing devices 10, a plurality of input devices 40 corresponding thereto, a collecting hopper 11, a packaging unit 12, and a control device 15.

The solid preparation dispensing device 10 includes a solid preparation accommodating portion 20 configured to accommodate the solid preparations 3, and is configured to discharge a desired number of solid preparations 3 in the solid preparation accommodating portion 20. In the solid preparation dispensing device 10, a number detection unit 32 configured to detect the number of discharged drugs is provided below the solid preparation accommodating portion 20.

The solid preparation accommodating portion 20 has, on its upper surface, a charging port 13 into which the solid preparations 3 are to be charged. The charging port 13 is provided with an upper lid (not shown) to be easily opened and closed.

The solid preparation dispensing device 10 is controlled by the control device 15, and discharges the solid preparations 3 on a dose-by-dose basis.

The solid preparation dispensing device 10 is capable of restricting a practical wideness (for example, height and width) of a dispensing passage for allowing the solid preparations 3 to pass therethrough, to thereby restrict the shape of the solid preparations which may pass through the dispensing passage, and is capable of handling a plurality of kinds of solid preparations 3. A configuration of the solid preparation dispensing device 10 is described later.

The input devices 40 each form an administration information input unit, and are provided to the solid preparation dispensing devices 10 on a one-to-one basis. In particular, in this embodiment, the input device 40 is integrated with the solid preparation dispensing device 10.

The input device 40 is configured to directly input an administration timing for the solid preparations 3 and a dosage for each administration timing in association with the solid preparations 3 charged into the solid preparation accommodating portion 20.

The input device 40 includes an input unit 41, for example, a keyboard, and a display unit 42.

Figures 6A, 6B:
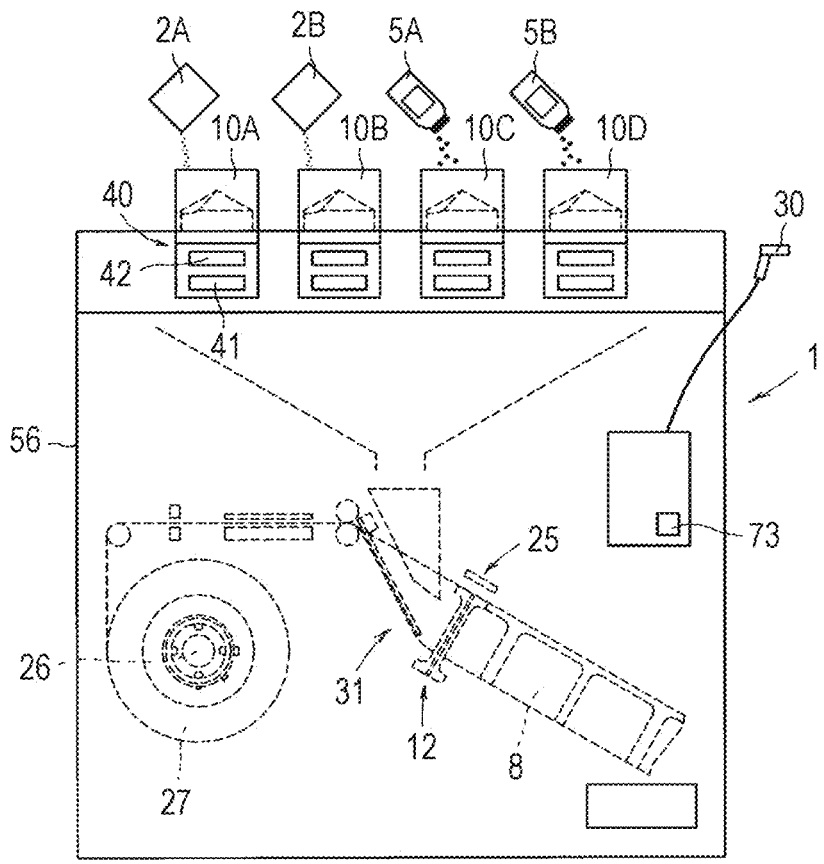
FIG. 6A is an external view of the solid preparation subdividing device according to the embodiment of this disclosure.
FIG. 6B is a display screen of an input device accompanying the solid preparation dispensing device.

A display screen 48 of the display unit 42 is, for example, as illustrated in FIG. 6B, and includes a name input field 43, a product name display field (solid preparation display field) 45, an administration timing designation field (timing field) 46, and an administration number input field (number input field) 47.

The name input field 43 is a field for inputting the name of a recipient or purchaser by operating the input unit 41, for example, a keyboard.

The product name display field 45 is a field for automatically displaying the product name or the like of the solid preparations 3 charged into the solid preparation accommodating portion 20 of the solid preparation dispensing device 10 based on information read by a solid preparation information reading unit 30 described later.

The administration timing designation field 46 includes the indications of "AFTER BREAKFAST", "AFTER LUNCH", "AFTER DINNER", and "BEFORE BEDTIME", and is a field for putting a check mark to a required administration timing by operating the input unit 41, for example, a keyboard. When "AFTER BREAKFAST", "AFTER LUNCH", "AFTER DINNER", or "BEFORE BEDTIME" is clicked, the administration timing designation field 46 causes the indication to emit light or change its color to indicate that the clicked administration timing has been selected.

The administration number input field 47 is a field for inputting the number of solid preparations to be taken in association with each of "AFTER BREAKFAST", "AFTER LUNCH", "AFTER DINNER", and "BEFORE BEDTIME" in the administration timing designation field 46 described above.

The plurality of solid preparation dispensing devices 10 integrated with the input devices 40 are arranged in a horizontal row on the upper part side of a device main body 56 as illustrated in FIGS. 6A and 6B. When the number of solid preparation dispensing devices 10 is large, the solid preparation dispensing devices 10 are arrayed in a plurality of stages so that the solid preparation dispensing devices 10 are arranged in a three-dimensional arrangement.

The collection hopper 11 is provided below the group of solid preparation dispensing devices, and is configured to collect the solid preparations 3 discharged from the solid preparation dispensing devices 10 and supply the solid preparations 3 to the packaging unit 12.

The packaging unit 12 includes a printing portion 22, a bag-portion forming mechanism 31, and a partition forming device 25 as in FIGS. 6A and 6B. The partition forming device 25 functions also as a sheet feeding mechanism.

The sheet feeding mechanism is a device configured to pay out a sheet-like drug package paper 27 wound around a roll shaft 26 and feed the drug package paper 27 to a printing portion 22 and the bag-portion forming mechanism (not shown) on a downstream side.

In this embodiment, the drug package paper 27 is folded in half in advance, and is wound in a roll shape.

The printing portion 22 is configured to print predetermined information on the drug package paper 27.

In this embodiment, information such as a recipient name, a drug name or a supplement name, and an administration timing such as "AFTER BREAKFAST" or "AFTER LUNCH" is printed on the drug package paper 27.

The bag-portion forming mechanism 31 is configured to form a bag portion with open one end by placing a plate (not shown) onto the half-folded drug package paper 27 and opening one side of the drug package paper 27 (upper side in the drawing). A lower portion of the collection hopper 11 is open to an inside of the bag portion of the drug package paper 27, which is formed by the bag-portion forming mechanism (not shown).

The partition forming device 25 is a heat seal device. The partition forming device 25 is driven by a motor (not shown), and is configured to form bags (packages) 8 by partitioning the bag portion to divide the bag portion into individual bag portions on a package-by-package basis.

A sheet discharge port 33 is provided at the lower part of the device main body 56. The solid preparations 3 (bag 8) individually packaged by the packaging unit 12 are discharged from the sheet discharge port 33.

The control device 15 is a device configured to control components of the solid preparation subdividing device 1.

A solid preparation information reading unit 30 is mounted to the control device 15. The solid preparation information reading unit 30 is, for example, a barcode reader or a device configured to read information written in an IC chip. In this embodiment, a barcode reader is adopted as the solid preparation information reading unit 30. That is, the solid preparation information reading unit 30 is a bar code reader serving as an image reading unit. The solid preparation information reading unit 30 is not limited to the bar code reader, and may be configured to read information on an IC chip. The solid preparation information reading unit 30 may be further configured to analyze a character.

Next, functions of the solid preparation subdividing device 1 according to this embodiment are described along a procedure of use.

As described above, the solid preparation subdividing device 1 according to this embodiment is a device configured to subdivide the solid preparations 3 sold by being filled in the small containers, for example, the package pouch 2, in accordance with use timings and further individually package the solid preparations 3.

When the solid preparation subdividing device 1 is used, information recorded in the two-dimensional barcode (information recording portion) 7 provided to the labels 17 of the package pouch 2 is read through use of the solid preparation information reading unit 30. Further, when identification information is present, the identification information is also read through use of the solid preparation information reading unit 30.

Then, the package pouch 2 or the bottle 5 is opened, and the solid preparations 3 therein are charged into one solid preparation dispensing device 10. That is, all the solid preparations 3 in one package pouch 2 or the like are charged into the solid preparation accommodating portion 20 of one solid preparation dispensing device 10.

The solid preparations 3 are charged into the solid preparation accommodating portion 20 from the charging port 13 provided to the upper surface of the solid preparation accommodating portion 20. In this embodiment, the charging port 13 is provided with the upper lid to be easily opened and closed, and hence the upper lid is opened to charge the solid preparations 3 into the solid preparation accommodating portion 20.

For example, the solid preparation information reading unit 30 is used to read information recorded in the two-dimensional bar code (information recording portion) 7 provided on the label 17 of the package pouch 2A. Subsequently, the package pouch 2A is opened, and the solid preparations 3 therein are charged into the solid preparation dispensing device 10.

In the same manner, the solid preparation information reading unit 30 is used to read information provided on the label 17 of each package pouch 2B. Subsequently, the package pouch 2B is opened, and all the solid preparations 3 in the package pouch 2B are charged into the solid preparation accommodating portion 20 of the solid preparation dispensing device 10B.

The same applies to a bottle A and a bottle B. That is, the solid preparation information reading unit 30 is used to read the information provided on the labels 17, and all the solid preparations 3 in the bottle A and the bottle B are charged into the solid preparation accommodating portions 20 of the solid preparation dispensing devices 10C and 10D, respectively.

Then, the input device 40 accompanying each solid preparation dispensing device 10 is operated to directly input, for each kind of solid preparation 3, the administration timing for the solid preparations 3 and the dosage for each administration timing.

In this embodiment, the input device 40 serving as the administration information input unit is capable of directly inputting the administration timing for the solid preparations 3 and the dosage for each administration timing in association with the solid preparations 3 charged into the solid preparation accommodating portion 20.

For example, the input unit 41, for example, a keyboard is operated to input an own name "HIRAGA GENNAI" in the name input field 43 of an input device 40A accompanying the solid preparation dispensing device 10A. In the product name display field 45 of the input device 40A, the product name "VITAMIN SUPPLEMENT" of the solid preparations 3 charged into the solid preparation accommodating portion 20 of the solid preparation dispensing device 10A is automatically displayed based on the information read by the solid preparation information reading unit 30.

The administration timing designation field 46 includes the fields of "AFTER BREAKFAST", "AFTER LUNCH", "AFTER DINNER", and "BEFORE BEDTIME", and the input unit 41, for example, a keyboard is operated to put check marks to, for example, "AFTER BREAKFAST", "AFTER LUNCH", and "AFTER DINNER".

In the administration number input field 47, for example, "1" is input to the item "AFTER BREAKFAST", "2" is input to the item "AFTER LUNCH", and, for example, "2" is input to the item "AFTER DINNER".

In this embodiment, the display screen 48 is a dedicated screen for the solid preparations 3 contained in one solid preparation dispensing device 10A, and hence the administration timing for the solid preparations 3 and the dosage for each administration timing are directly input in association with the solid preparations 3 charged into the solid preparation accommodating portion 20.

In the name input field 43 of the input device 40B accompanying the solid preparation dispensing device 10B, the name previously input by the input device 40A is automatically displayed. Further, in the product name display field 45 of the input device 40B, the product name "FISH COMPONENT SUPPLEMENT" of the solid preparations 3 charged into the solid preparation accommodating portion 20 of the solid preparation dispensing device 10B is automatically displayed based on the information read by the solid preparation information reading unit 30.

The administration timing designation field 46 includes the fields of "AFTER BREAKFAST", "AFTER LUNCH", "AFTER DINNER", and "BEFORE BEDTIME", and the input unit 41, for example, a keyboard is operated to put check marks to, for example, "AFTER BREAKFAST", and "AFTER LUNCH".

In the administration number input field 47, for example, "2" is input to the item "AFTER BREAKFAST", and, for example, "2" is input to the item "AFTER LUNCH".

In the name input field 43 of the input device 40C accompanying the solid preparation dispensing device 10C, the name previously input by the input device 40A is automatically displayed. Further, in the product name display field 45 of the input device 40C, the product name "ZINC SUPPLEMENT" of the solid preparations 3 charged into the solid preparation accommodating portion 20 of the solid preparation dispensing device 10C is automatically displayed based on the information read by the solid preparation information reading unit 30.

The administration timing designation field 46 includes the fields of "AFTER BREAKFAST", "AFTER LUNCH", "AFTER DINNER", and "BEFORE BEDTIME", and the input unit 41, for example, a keyboard is operated to put check marks to, for example, "AFTER BREAKFAST" and "BEFORE BEDTIME".

In the administration number input field 47, for example, "1" is input to the item "AFTER BREAKFAST", and, for example, "1" is input to the item "BEFORE BEDTIME".

In the name input field 43 of the input device 40D accompanying the solid preparation dispensing device 10D, the name previously input by the input device 40A is automatically displayed. Further, in the product name display field 45 of the input device 40D, the product name "GARLIC SUPPLEMENT" of the solid preparations 3 charged into the solid preparation accommodating portion 20 of the solid preparation dispensing device 10D is automatically displayed based on the information read by the solid preparation information reading unit 30.

The administration timing designation field 46 includes the fields of "AFTER BREAKFAST", "AFTER LUNCH", "AFTER DINNER", and "BEFORE BEDTIME", and the input unit 41, for example, a keyboard is operated to put check marks to, for example, "AFTER BREAKFAST" and "BEFORE BEDTIME".

In the administration number input field 47, for example, "1" is input to the item "AFTER BREAKFAST", and, for example, "2" is input to the item "BEFORE BEDTIME".

When the operation of charging the solid preparations 3 and inputting required items to the input device 40 is finished, a start switch (not shown) is operated so as to start subdividing operations.

The solid preparation dispensing device 10 includes a form changing unit configured to change its form so that the solid preparations 3 can be smoothly discharged depending on its shape, and can support a plurality of kinds of solid preparations 3. In the solid preparation subdividing device 1 according to this embodiment, the form changing unit functions first.

In this case, the shape of the solid preparation 3 can be identified from the information read by the solid preparation information reading unit 30, and it is known which solid preparation 3 has been charged into each solid preparation dispensing device 10. Therefore, each solid preparation dispensing device 10 changes its form in accordance with the shape of the charged solid preparation 3.

Then, the solid preparations 3 are actually subdivided.

For example, in accordance with the example described above, as the solid preparation 3 to be taken after breakfast, one tablet of the "VITAMIN SUPPLEMENT" having been charged from the solid preparation dispensing device 10A into the package pouch 2A is discharged, and two tablets of the "FISH COMPONENT SUPPLEMENT" having been charged from the solid preparation dispensing device 10B into the package pouch 2B are discharged.

Further, one tablet of "ZINC" having been charged from the solid preparation dispensing device 10C into the bottle 5A is discharged, and one tablet of "GARLIC SUPPLEMENT" having been charged from the solid preparation dispensing device 10D into the bottle 5B is discharged.

The solid preparations 3 for one administration, which have been discharged from the solid preparation dispensing devices 10 and are to be taken after breakfast, are collected by the collection hopper 11 and delivered to the packaging unit 12. Then, all of the solid preparations 3 are placed in one bag portion of the drug package paper 27 formed by the bag-portion forming mechanism 31.

Moreover, prior to the placement of the solid preparations 3, required information is printed on the bag portion by the printing portion 22 provided on the upstream side.

That is, characters of "HIRAGA GENNAI" are printed as an indication for identifying a recipient. Moreover, as an indication of an administration timing, characters of "AFTER BREAKFAST" are printed. Further, as required, kinds and numbers of the solid preparations 3 to be packaged are printed.

The bag portion having the solid preparations 3 charged therein is delivered to a partition forming device (heat seal device) 25 provided on the downstream side, and is partitioned into an independent bag (package) 8 with three sides thereof being thermally fused.

Subsequently, the series of individual packaging operations described above are automatically repeated. That is, solid preparations 3 corresponding to the next administration timing are discharged from the solid preparation dispensing devices 10 and delivered to the packaging unit 12 via the collection hopper 11, and all of the solid preparations 3 are placed in one bag of the drug package paper 27.

Further, prior to this operation, required information is printed on the bag portion by the printing portion 22 provided on the upstream side.

Specifically, the next administration timing is after lunch, and hence, as the solid preparations 3 to be taken after lunch, two tablets of "VITAMIN SUPPLEMENT" filled in the package pouch 2A are discharged from the solid preparation dispensing device 10A, and two tablets of "FISH COMPONENT SUPPLEMENT" filled in the package pouch 2B are discharged from the solid preparation dispensing device 10B.

From the solid preparation dispensing device 10C, no tablets of "ZINC SUPPLEMENT" are discharged. From the solid preparation dispensing device 10D, no tablets of "GARLIC SUPPLEMENT" are discharged.

Further, characters of "HIRAGA GENNAI" are printed on the bag portion as an indication for identifying a recipient. Further, as an indication of an administration timing, an indication of "AFTER LUNCH" is printed.

Next, solid preparations 3 to be taken after dinner are discharged from the solid preparation dispensing devices 10 and packaged in one bag portion by the packaging unit 12. Specifically, two tablets of "VITAMIN SUPPLEMENT" are discharged from the solid preparation dispensing device 10A and packaged. Other solid preparations are not discharged.

Subsequently, solid preparations 3 to be taken before bedtime are discharged from the respective solid preparation dispensing devices 10 and packaged in one bag portion by the packaging unit 12. Specifically, one tablet of "ZINC SUPPLEMENT" filled in the bottle 5A is discharged from the solid preparation dispensing device 10C, and two tablets of "GARLIC SUPPLEMENT" filled in the bottle 5B are discharged from the solid preparation dispensing device 10D.

When solid preparations 3 to be taken in the order of "AFTER BREAKFAST", "AFTER LUNCH", "AFTER DINNER", and "BEFORE BEDTIME" are enclosed in respective bags 8, and packaging of solid preparations for one day is completed, solid preparations 3 to be taken "AFTER BREAKFAST", "AFTER LUNCH", and "AFTER DINNER" of the next day are sequentially enclosed in respective bags 8. In such a manner, the subdividing operations are continued until all of the solid preparations 3 in the solid preparation dispensing devices 10 are discharged.

The bags 8 are discharged from the sheet discharge port 33 under a state of being connected in a belt form.

When there is any excess or shortage of the solid preparations 3 filled in the package pouches, and the solid preparations 3 to be enclosed in one bag 8 are insufficient, the subdividing operations are interrupted, and this fact is displayed on the monitor (not shown).

For example, even though solid preparations 3 for two weeks are filled in the package pouches 2A and 2B, and the bottle 5A, when solid preparations 3 for only ten days are filled in the bottle 5B, the subdividing operations are interrupted at the timing of completion of bags 8 for ten days, and this fact is displayed on the display portion.

A user can restart the subdividing operations while knowing that there is shortage, or can discharge the remaining solid preparations 3 and collect the same in the package pouches 2A and 2B, and the bottle 5A. This selection is performed through manual operation on the input unit (not shown) of the control device 15. Alternatively, the selection may be performed in accordance with setting input in advance.

In the embodiment described above, all the solid preparations 3 charged into the solid preparation dispensing devices 10 are supplements or drugs which are available for the public. However, this disclosure is not limited to this configuration, and those prepared for individual use may be mixed.

For example, gastrointestinal drugs, vitamin preparations, and the like prepared based on a prescription given by a doctor for use by individual patient may be charged into the solid preparation dispensing devices 10A and 10B, while supplements purchased based on a user's preference may be charged into the solid preparation dispensing devices 10C and 10D.

In the above-mentioned embodiment, "AFTER BREAKFAST", "AFTER LUNCH", "AFTER DINNER", and "BEFORE BEDTIME" are set as the administration timings, but this disclosure is not limited thereto. For example, "BEFORE BREAKFAST", "BEFORE OR AFTER LUNCH", and "AFTER DINNER" may be set. In addition, when the dosages of the solid preparations are small or when the kinds of solid preparations are few, the packaging may be performed in unit of "DAY" by collectively grouping the above-mentioned different administration timings. The unit of "DAY" may be classification based on days of the week such as "MONDAY", "TUESDAY", and "WEDNESDAY", or may be classification based on dates such as "JULY 1" or "JULY 2".

Content to be printed on a packaging paper sheet is appropriately changed depending on the administration timing in order to prevent mistakes in viewing or taking. For example, "BEFORE BREAKFAST", "BEFORE OR AFTER LUNCH", and "AFTER DINNER" are printed, or "Monday" and "Tuesday" are printed. In that case, the drug name, the recipient name, and the like are printed together as well.

Next, description is made of the solid preparation dispensing device 10. The solid preparation dispensing device 10 adopted in this embodiment includes the solid preparation accommodating portion 20, which is configured to accommodate the solid preparations 3, and is configured to discharge only a desired number of solid preparations 3 in the solid preparation accommodating portion 20.

Further, it is desired that the solid preparation dispensing device 10 adopted in this embodiment be capable of handling solid preparations 3 of various shapes and structures and discharging one or a plurality of solid preparations 3 at a time.

That is, the solid preparations 3 are roughly classified into a tablet and a capsule in terms of structure. Moreover, examples of the shape of the tablet include a flat circular shape, an elliptical shape, and a spherical shape. The size of the tablet varies. This similarly applies to the capsule, and the size of the capsule varies.

The solid preparation dispensing device 10 adopted in this embodiment includes the form changing unit configured to change the form so that the solid preparations 3 can be smoothly discharged depending on the shape of the solid preparation 3. Specifically, in order to be capable of handling solid preparations 3 of a plurality of shapes and structures, the solid preparation dispensing device 10 adopted in this embodiment increases or decreases the wideness of the dispensing passage for allowing the solid preparations 3 to pass therethrough to limit the shape of the solid preparation which may pass through the dispensing passage, thereby being capable of handling a plurality of kinds of solid preparations 3.

That is, in order to discharge one solid preparation 3 at a time, it is required that the solid preparations 3 be arrayed in a row at some positions. When the dispensing passage is wide, the plurality of solid preparations 3 are arrayed in parallel, and a plurality of solid preparations may be discharged at a time. In contrast, when the dispensing passage is narrow, the solid preparation 3 cannot pass through the dispensing passage, and hence the solid preparation 3 cannot be discharged.

Therefore, in order to discharge one solid preparation 3 at a time, it is required to change the size (wideness) of the dispensing passage in accordance with the solid preparations 3 to be stored.

The solid preparation dispensing device 10 in this embodiment is capable of suitably adjusting a height and a width of the dispensing passage by restricting the dispensing passage for the solid preparations 3. Thus, even when solid preparations 3 of any shape and size are charged into the solid preparation accommodating portion 20, a desired number of solid preparations 3 can be discharged without delay.

Now, description is made. The solid preparation dispensing device 10 includes, as illustrated in FIG. 3 and FIG. 4, the solid preparation accommodating portion 20 configured to accommodate a plurality of solid preparations 3, a first rotating member 50, and a second rotating member 51.

Figure 3:
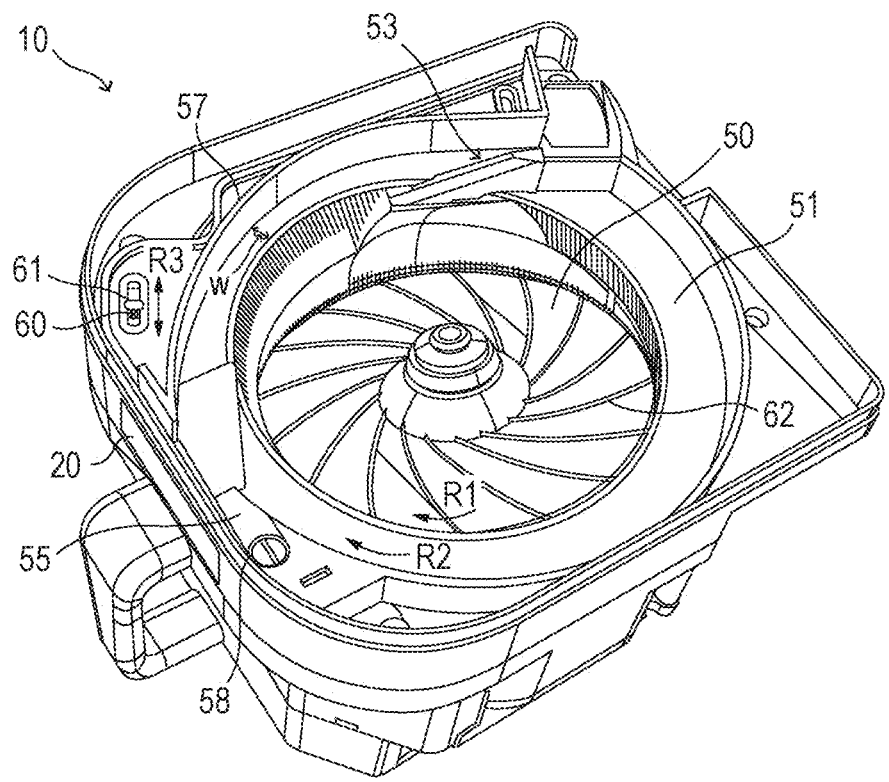
FIG. 3 is a perspective view for illustrating a solid preparation dispensing device adopted in the solid preparation subdividing device according to the embodiment of this disclosure, as viewed from one direction.
Figure 4:
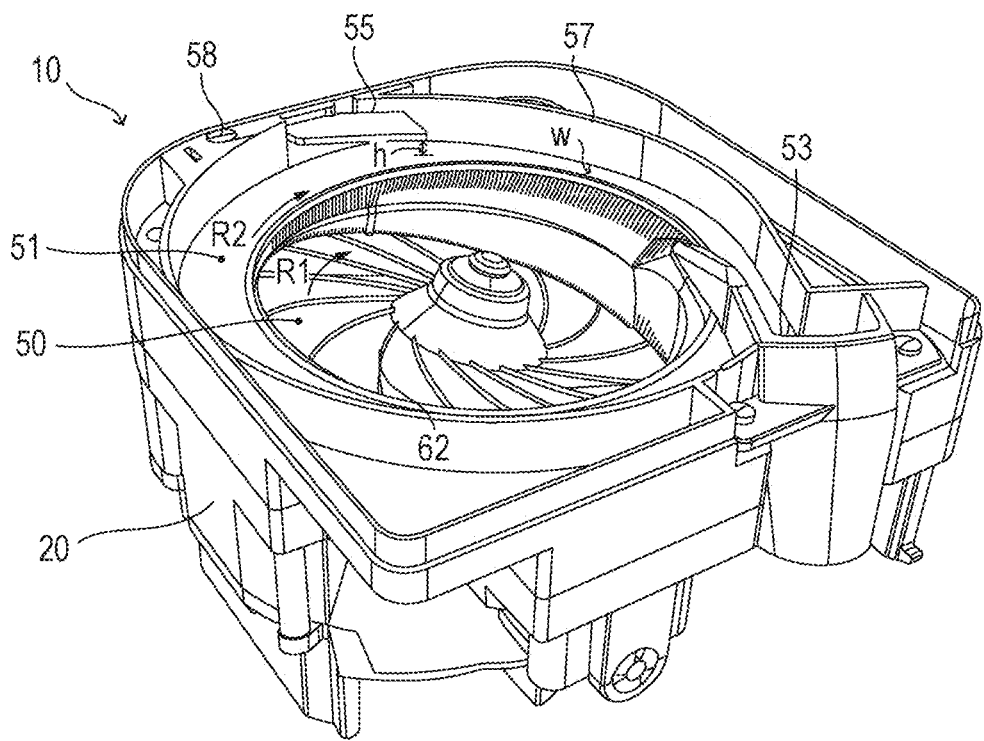
FIG. 4 is a perspective view for illustrating the solid preparation dispensing device of FIG. 3, as viewed from a different direction.
Figure 5:
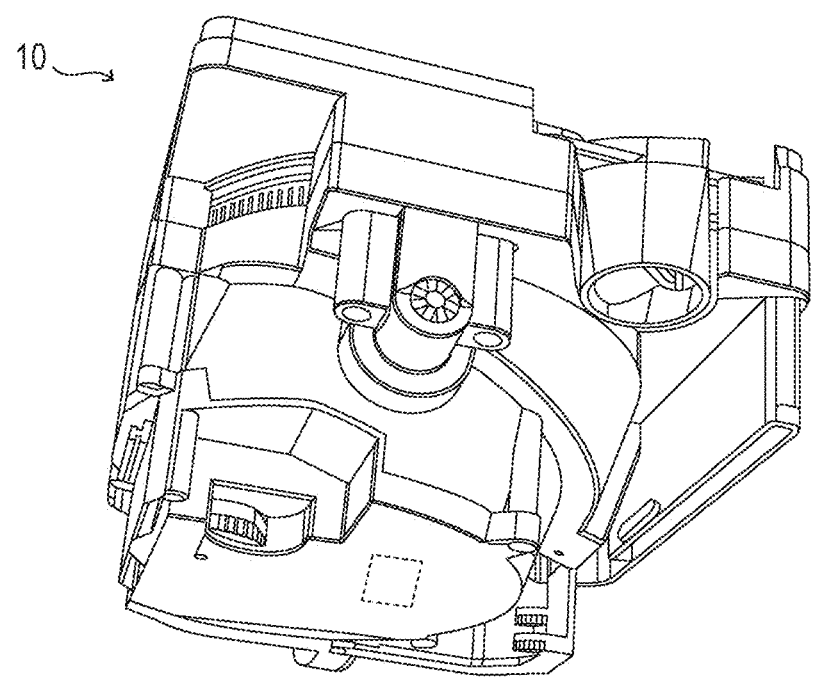
FIG. 5 is a perspective view for illustrating the solid preparation dispensing device of FIG. 3, as viewed from a lower side.

In FIG. 3 and FIG. 4, a cover member configured to cover an upper part is omitted.

The first rotating member 50 is a disc-shaped member forming a bottom surface of the solid preparation accommodating portion 20. A rotation axis of the first rotating member 50 is inclined by a predetermined angle with respect to a vertical direction so that an upper surface of the first rotating member 50 is inclined by a predetermined angle with respect to a horizontal plane. Further, radial ribs 62 are formed at predetermined intervals on the upper surface of the first rotating member 50.

The first rotating member 50 is rotatably supported by a housing of the solid preparation dispensing device 10, and is rotated by a motor (not shown). Further, the first rotating member 50 is raised and lowered.

The second rotating member 51 is a hollow annular member arranged around the first rotating member 50 in plan view. The second rotating member 51 is located on an upper side of the solid preparation accommodating portion 20. An upper end portion of the first rotating member 50 described above is located on the same horizontal plane as the second rotating member 51.

The second rotating member 51 is also rotatably supported by the housing of the solid preparation dispensing device 10, and is rotated by a motor (not shown).

A part of the second rotating member 51 is continuous with a discharge port 53 for discharging the solid preparation 3 from the solid preparation accommodating portion 20. Through the rotation of the second rotating member 51, the solid preparation 3 is conveyed to the discharge port 53. Thus, an upper part of the second rotating member 51 forms a part of the dispensing passage for allowing the solid preparation 3 to pass therethrough.

In this embodiment, on the dispensing passage for conveying the solid preparation 3 to the discharge port 53 by the second rotating member 51, there are arranged a height restriction member 55 and a width restriction member 57.

The height restriction member 55 is provided on the second rotating member 51, and is configured to restrict a height from a conveyance surface of the second rotating member 51. The height restriction member 55 is configured to restrict a height of an object passing this part. The height restriction member 55 is configured to restrict the size of the solid preparation 3, which can be conveyed to the discharge port 53 by the second rotating member 51, in a height direction.

Meanwhile, the width restriction member 57 protrudes from a side of the second rotating member 51 toward a region (dispensing passage) of the second rotating member 51, and is configured to temporarily reduce a width of a conveyance passage of the second rotating member 51. The width restriction member 57 is configured to restrict, through use of the second rotating member 51, the size of the solid preparations 3 which can be conveyed to the discharge port 53.

With this configuration, in the solid preparation dispensing device 10, among tablets placed on the second rotating member 51, only tablets having the size within a height "h" restricted by the height restriction member 55 and a width "w" restricted by the width restriction member 57 are dispensed from the discharge port 53. Thus, in the solid preparation dispensing device 10, when the height and the width of one tablet accommodated in the solid preparation accommodating portion 20 satisfy the height "h" and the width "w", the tablet can be dispensed on a one-by-one basis.

The width restriction member 57 is supported so as to be rotatable about a perpendicular axis (not shown) with respect to the housing of the solid preparation dispensing device 10. The width restriction member 57 turns in the horizontal direction through driving of a motor (not shown), to thereby change a projection amount of the width restriction member 57 toward the solid preparation accommodating portion 20 side (region of the second rotating member 51) and change the width "w" restricted by the width restriction member 57.

That is, the solid preparation dispensing device 10 includes a width adjustment member 60 configured to change the width "w" restricted by the width restriction member 57. A pinion gear is formed on an outer peripheral surface of the width adjustment member 60, and is engaged with a rack (gear) formed on an inner peripheral surface of an elongated hole 61 formed in the width restriction member 57.

The projection amount of the width restriction member 57 toward the solid preparation accommodating portion 20 side is changed by relative movement of the width adjustment member 60 and the elongated hole 61 in the arrow R3 direction (see FIG. 3) by the rotation of the width adjustment member 60.

Further, the solid preparation dispensing device 10 includes a height adjustment portion 58 configured to change the height "h" restricted by the height restriction member 55.

The height adjustment portion 58 is rotatably supported on the housing of the solid preparation dispensing device 10. The height adjustment portion 58 is rotated by a motor (not shown) so that a position of a lower end portion thereof is moved in an up-and-down direction, to thereby change the height "h" restricted by the height restriction member 55.

In the solid preparation dispensing device 10 of this embodiment, the first rotating member 50 and the second rotating member 51 are rotated by a motor (not shown). Further, the first rotating member 50 is raised and lowered in the solid preparation accommodating portion 20. When the solid preparations 3 in the solid preparation dispensing device 10 are to be discharged, the first rotating member 50 and the second rotating member 51 are rotated. When the first rotating member 50 is rotated in the rotation direction R1 (see FIG. 3 and FIG. 4), tablets in the solid preparation accommodating portion 20 are discharged from the first rotating member 50 to the second rotating member 51. Further, when the second rotating member 51 is rotated in the rotation direction R2 (see FIG. 3 and FIG. 4), tablets on the second rotating member 51 are conveyed toward the discharge port 53.

However, in this embodiment, the dispensing passage for the solid preparations 3 is restricted by the height restriction member 55 and the width restriction member 57, and hence the height and the width are restricted. Therefore, among the solid preparations 3 conveyed by the second rotating member 51, tablets stacked in the height direction are brought into contact with the height restriction member 55 and returned to the solid preparation accommodating portion 20. Further, among the tablets conveyed by the second rotating member 51, the solid preparations 3 arrayed in the width direction are brought into contact with the width restriction member 57 and returned to the solid preparation accommodating portion 20.

Thus, in the solid preparation dispensing device 10 of this embodiment, tablets having the size corresponding to the height "h" restricted by the height restriction member 55 and the width "w" restricted by the width restriction member 57 are conveyed to the discharge port 53 in a state of being aligned on a one-by-one basis in the circumferential direction on the second rotating member 51. Therefore, in the solid preparation dispensing device 10, the tablets accommodated in the solid preparation accommodating portion 20 can be dispensed on a one-by-one basis, to thereby be capable of controlling the dispensing amount of the tablets.

For example, it is desired that master data on each solid preparation 3 be stored in the control device 15 of the solid preparation subdividing device 1 or a host control device, and that shape information (dimensions) of the solid preparation 3 be registered in the master data in advance.

The solid preparation 3 is identified from the information detected by the solid preparation information reading unit 30, and is compared against the master data to acquire information related to the shape of the solid preparation 3 charged into the solid preparation dispensing device 10.

Then, the form changing unit is caused to function based on the acquired shape information of the solid preparation 3 so as to adjust the height and the width of the dispensing passage. An appropriate dispensing speed is determined. In this embodiment, the rotation speed of the second rotating member 51 is determined.

Meanwhile, when the master data includes no shape information of the solid preparation 3, the form changing unit is functioned to find out an appropriate size of the dispensing passage. Specifically, the dispensing passage (width and height) is increased stepwise, and the width of the passage through which the solid preparation 2 is to pass is sought to determine the size of the passage. Then, information on the dispensing passage at this time is stored in the master data as the shape information, and the form changing unit is controlled by referring to this information from the next time onward.

When there is no master data itself or when there is no unit configured to store the master data, the above-mentioned work of finding out the appropriate size of the dispensing passage is performed each time the solid preparation 3 is charged into the solid preparation dispensing device 10.

The solid preparation dispensing device 10 described above restricts both the height and the width of the passage for allowing the solid preparation 3 to pass therethrough. However, the solid preparation dispensing device 10 may restrict only one of the height and the width.

Moreover, this disclosure may have a configuration in which the dispensing passage for the solid preparations 3 is fixed and the height and the width cannot be changed.

The solid preparation dispensing device 10 may have a configuration in which a rotor is provided in the solid preparation accommodating portion 20 as disclosed in, for example, Patent Literature 2. The rotor has a vertical groove, and the solid preparations 3 are fitted to the vertical groove. Further, through rotation of the rotor, the vertical groove reaches a position of the discharge port, and the solid preparations 3 fitted in the vertical groove are discharged from the solid preparation accommodating portion 20.

The solid preparation pickup unit is not limited to the configuration described above, and may be configured to push out solid preparations one by one through use of, for example, a pusher.

Moreover, the solid preparation pickup unit may be configured to discharge the solid preparations one by one through use of vibration. For example, the solid preparation pickup unit may have the following structure. A guide track for allowing the solid preparations to proceed is provided, and the guide track is vibrated to transfer the solid preparations along the guide track.

Next, an example of a store using the solid preparation subdividing device 1 according to this embodiment is described.

The solid preparation subdividing device 1 is installed in such a drugstore as illustrated in, for example, FIG. 7. In the drugstore, a display shelf 70 and a checkout counter 71 are installed in addition to the solid preparation subdividing device 1.

Various supplements are displayed on the display shelf 70 for sale. The supplements are filled in the packaging materials 6 such as the package pouches 2 and the bottles 5.

A purchaser picks out his/her favorite supplements from the display shelf 70, and proceeds to the solid preparation subdividing device 1 with their packaging materials 6. Then, the purchaser opens the package pouches 2 and the bottles 5 to charge the solid preparations (supplements) 3 into their separate solid preparation accommodating portions 20.

Immediately after the solid preparations 3 are charged, the solid preparation information reading unit 30 is used to read the information recorded in the two-dimensional bar code (information recording portion) 7 provided on the label 17 of each of the package pouches 2 and the like.

Then, a series of subdividing operations are performed in the above-mentioned manner. The subdivided solid preparations 3 are discharged from the sheet discharge port 33 under a state of being connected in a continuous sheet form.

The purchaser brings the solid preparations 3 connected in a continuous sheet form together with the empty package pouches 2 and the empty bottles 5 to the checkout counter 71, and pays the total price.

The payment (decision) of the total price may be performed before the package pouches 2 and the bottles 5 are selected and opened.

In another case, the solid preparation subdividing device 1 may be installed in the checkout counter 71 to allow a store clerk to open the package pouches 2 and the bottles 5 and perform subdividing work.

In this case, the operation of the input device 40 may be performed by the store clerk. For example, an experienced store clerk or pharmacist may give the purchaser advice on the administration timing and the dosage based on the purchaser's request, and the purchaser or the store clerk may perform predetermined input.

In the above-mentioned embodiment, the plurality of input devices 40 are provided in association with the solid preparation dispensing devices 10, but required items may be input from one input device.

For example, a screen of a personal computer is used to input the required items on each screen while switching the display screen.

In short, it suffices that the administration information input unit includes a display screen, on which the solid preparation display field for identifying the solid preparation and the timing field for displaying the administration timing of the solid preparations are displayed in association with each other along with the number input field provided in association with those fields to allow the number to be input to the number input field.

Further, a past input history may be stored in a storage unit 73 of the control device 15 in advance, and may be called as the requirement arises to cause the above-mentioned series of individual packaging operations to be performed.

For example, when the purchaser visits the drugstore on another day to select the same solid preparations 3 purchased previously and read the information of each of the package pouches 2 and the like by the solid preparation information reading unit 30, the administration information left in the memory is automatically displayed on the display screen 48 of the display unit 42. When the purchaser performs no correction, the series of individual packaging operations are executed again based on the information stored in the storage unit 73.

The invention claimed is:

1. A solid preparation subdividing device configured to subdivide a plurality of solid preparations on a dose-by-dose basis, the solid preparation subdividing device comprising:
   a plurality of solid preparation dispensing devices;
   a solid preparation information input unit;
   a plurality of administration information input units, each administration information input unit corresponding to one of the plurality of solid preparation dispensing devices; and
   a packaging unit, wherein
   each solid preparation dispensing device includes:
      a solid preparation accommodating portion comprising a charging port into which the plurality of solid preparations is to be charged; and
      a solid preparation pickup unit configured to discharge a predetermined number of solid preparations from the solid preparation accommodating portion,
   the solid preparation information input unit is configured to receive first information for identifying the plurality of solid preparations charged into the solid preparation accommodating portion of each solid preparation dispensing device,
   each administration information input unit is configured to receive second information including an administration timing for each of the plurality of solid preparations and a dosage for each administration timing in association with the plurality of solid preparations charged into the solid preparation accommodating portion of the corresponding solid preparation dispensing device, and
   the solid preparation subdividing device is configured to execute a series of individual packaging operations for discharging, based on the second information input to each administration information input unit, the plurality of solid preparations from the corresponding solid preparation dispensing device on a dose-by-dose basis to send out the plurality of solid preparations to the packaging unit for packaging by the packaging unit.

2. The solid preparation subdividing device according to claim 1, further comprising:
   a printing unit, configured to perform a predetermined printing on a package corresponding to a dose.

3. The solid preparation subdividing device according to claim 1, wherein
   each solid preparation dispensing device further includes a form changing unit configured to change a form so as to discharge each of the plurality of solid preparations depending on a respective shape of said each of the plurality of solid preparations.

4. The solid preparation subdividing device according to claim 3, wherein
   the form changing unit is configured to change the form based on the first information input into the corresponding solid preparation information input unit.

5. The solid preparation subdividing device according to claim 3, further comprising:
   a dispensing passage configured to allow the plurality of solid preparations to pass therethrough,
   wherein
   the form changing unit is configured to restrict a shape of a solid preparation allowed to pass through the dispensing passage by changing a state of the dispensing passage, and
   the solid preparation subdividing device is configured to change the state of the dispensing passage based on the first information input into each solid preparation information input unit, to thereby enable the plurality of solid preparations accommodated in the solid preparation accommodating portion of the corresponding solid preparation dispensing device to be discharged.

6. The solid preparation subdividing device according to claim 1, wherein
   each administration information input unit comprises at least one input device, and
   the solid preparation subdividing device is further configured to:

identify each of the plurality of solid preparations when input is performed from the input device of any of the plurality of administration information input units, and cause the administration timing for each of the plurality of solid preparations and the dosage for each administration timing to be directly input in association with each other using the input device of the corresponding administration information input unit.

7. The solid preparation subdividing device according to claim 1, wherein each administration information input unit is mounted to the corresponding solid preparation dispensing device.

8. The solid preparation subdividing device according to claim 1, wherein each administration information input unit comprises a display screen on which a solid preparation display field for identifying each of the plurality of solid preparations, and a timing field for displaying the administration timing for each of the plurality of solid preparations are displayed in association with each other with a number input field corresponding to the administration timing to receive a number to be input to the number input field.

9. The solid preparation subdividing device according to claim 1, wherein each solid preparation information input unit comprises a reading unit.

10. The solid preparation subdividing device according to claim 1, further comprising:

a storage unit configured to store third information for identifying a recipient and the second information input to each administration information input unit in association with the first information input to the corresponding solid preparation information input unit, wherein the solid preparation subdividing device is configured to execute the series of individual packaging operations based on information stored in the storage unit when solid preparations are charged from the charging port into each solid preparation accommodating portion after the series of individual packaging operations is executed and the corresponding solid preparation information input unit receives information for identifying the solid preparations again charged from the charging port into the corresponding solid preparation accommodating portion.

11. The solid preparation subdividing device according to claim 1, wherein when different solid preparations having the same administration timing are charged into the plurality of solid preparation dispensing devices, at least one of the plurality of solid preparation dispensing devices is configured to enclose the different solid preparations having the same administration timing in the same package.

12. The solid preparation subdividing device according to claim 1, wherein the solid preparation subdividing device is further configured to execute a series of individual packaging operations for packaging a plurality of kinds of solid preparations taken at a time collectively by the packaging unit.

13. The solid preparation subdividing device according to claim 1, wherein the plurality of solid preparations is a plurality of supplements.

14. A method comprising:

receiving a selection of at least one of a plurality of solid preparations from among a plurality of kinds of packages containing solid preparations;

opening a selected packaging material containing the selected solid preparations and retrieving the solid preparations contained therein;

automatically subdividing the retrieved solid preparations based on administration timing and then re-packaging the subdivided solid preparations;

calculating a total price of the selected solid preparations; and using the solid preparation subdividing device of claim 1 to charge the selected and removed solid preparations into the solid preparation subdividing device and then subdividing the solid drugs for each administration timing.

15. A method comprising:

receiving a selection of a plurality of packages, each package containing a plurality of solid preparations from among a plurality of kinds of packages containing solid preparations;

opening a selected packaging material of each selected package containing the selected solid preparations and transferring the solid preparations contained therein to a corresponding one of a plurality of solid preparation dispensing devices;

receiving, from each of a plurality of administration information input units, each administration information input unit corresponding to one of the plurality of solid preparation dispensing devices, an administration timing;

automatically subdividing the transferred solid preparations based on the corresponding administration timing and then re-packaging the subdivided solid preparations; and calculating a total price of the selected solid preparations.

16. The solid preparation sales method according to claim 15, wherein said subdividing comprises using the plurality of solid preparation subdividing devices, and the method further comprises charging the transferred solid preparations into the solid preparation subdividing device which then subdivides the charged solid preparations on a dose-by-dose basis for each administration timing.

* * * * *